US008598114B2

(12) United States Patent
Stensen et al.

(10) Patent No.: US 8,598,114 B2
(45) Date of Patent: Dec. 3, 2013

(54) ANTIMICROBIAL COMPOUNDS

(75) Inventors: Wenche Stensen, Kvaloysletta (NO);
Bengt Erick Haug, Tortnes (NO);
Oystein Rekdal, Hvalstad (NO); John Sigurd Svendsen, Kvaloysletta (NO)

(73) Assignee: Lytix Biopharma AS, Tromso (NO)

( * ) Notice: Subject to any disclaimer, the term of this patent is extended or adjusted under 35 U.S.C. 154(b) by 312 days.

(21) Appl. No.: 12/808,941

(22) PCT Filed: Dec. 22, 2008

(86) PCT No.: PCT/GB2008/004245
§ 371 (c)(1),
(2), (4) Date: Mar. 7, 2011

(87) PCT Pub. No.: WO2009/081152
PCT Pub. Date: Jul. 2, 2009

(65) Prior Publication Data
US 2011/0172145 A1    Jul. 14, 2011

(30) Foreign Application Priority Data

Dec. 20, 2007  (GB) .................................. 0724951.9

(51) Int. Cl.
*A01N 37/18* (2006.01)
*A61K 38/00* (2006.01)
*A61P 31/10* (2006.01)

(52) U.S. Cl.
USPC ........................................................ 514/3.3

(58) Field of Classification Search
None
See application file for complete search history.

(56) References Cited

U.S. PATENT DOCUMENTS

2002/0035239 A1 * 3/2002 Andersen et al. ............. 530/324
2007/0072808 A1   3/2007 Shai et al.

FOREIGN PATENT DOCUMENTS

| WO | 01/66147 | 9/2001 |
| WO | 03097664 A2 | 11/2003 |
| WO | 2004/110341 A2 | 12/2004 |
| WO | 2006086321 A2 | 8/2006 |

OTHER PUBLICATIONS

Svenson et al., J. Med. Chem. 2007, 50, 3334-3339.*
Haug et al., Peptide Science vol. 71, Issue 3, P022, p. 310, Article first published online: Jun. 23, 2003.*
Haug, et al. "Bulky Nonproteinogenic Amino Acids Permit the Design of Very Small and Effective Cationic Antibacterial Peptides." J Med Chem 47(17): 4159-4162. (2004).
Strom, et al. "The Pharmacophore of Short Cationic Antibacterial Peptides." J Med Chem 46(9): 1567-1570. (2003).
Bengt Erik Haug., "Antibacterial peptides containing non-coded aromatic amino acids," University of Tromso, XP007909093 (Chapter 4.6 and Paper IV) (May 2002).
Svenson et al., "Albumin binding of short cationic antimicrobial micropeptides and its influence on the in vitro bactericidal effect," J. Med. Chem. (2007): vol. 50, No. 14; pp. 3334-3339.
Svenson et al.,"Antimicrobial peptides with stability toward tryptic degradation," Biochemistry (Mar. 25, 2008): vol. 47, No. 12; pp. 3777-3788.
Haug et al., "Synthetic antimicrobial peptidomimetics with therapeutic potential," J. Med. Chem (2008): vol. 51, No. 14; pp. 4306-4314.
Haug et al., "Application of the Suzuki-Miyaura cross-coupling to increase antimicrobial potency generates promising novel antibacterials," Bioorganic & Medicinal Chemistry Letters (2007): vol. 17, No. 8; pp. 2361-2364.
International Search Report and Written Opinion issued for PCT/GB2008/004245.
Cirioni et al., "The lipopeptides Pal-Lys-Lys-NH2 and Pal-Lys-Lys soaking alone and in combination with intraperitoneal vancomycin prevent vascular graft biofilm in a subcutaneous rat pouch model of *Staphylococcal* infection", Peptides, Elsevier, Amsterdam, vol. 28, No. 6, Jun. 1, 2007, pp. 1299-1303.
Wei et al., "Effect of MUC7 peptides on the growth of bacteria and on *Streptococcus* mutans biofilm", JAC, vol. 57, Apr. 4, 2006, pp. 1100-1109.
Beckloff et al., "Activity of an Antimicrobial Peptide Mimetic against Planktonic and Biofilm Cultures of Oral Pathogens", Antimicrob. Agents Chemother, vol. 51, Sep. 4, 2007, pp. 4125-4132.
Haug et al., "The medicinal chemistry of short lactoferricin-based antibacterial peptides", Curr. Med. Chem, vol. 14, 2007, pp. 1-18.
Altman et al., "In vitro assessment of antimicrobial peptides as potential agents against several oral bacteria", JAC, vol. 58, May 10, 2006, pp. 198-201.
Eckert et al., "Targeted killing of *Streptococcus* mutans by a pheromone-guided "smart" Antimicrobial Peptide", Antimicrobial Agents Chemother, vol. 50, Oct. 23, 2006, pp. 3651-3657.
Lasa, "Towards the identification of the common features of bacterial biofilm development", International Microbiol, vol. 9, 2006, pp. 21-28.
Donlan et al., "Biofilms: Survival Mechanisms of Clinically Relevant Microorganisms", Clinical Microbiol, vol. 15, 2002, pp. 167-193.

* cited by examiner

*Primary Examiner* — Marcela M Cordero Garcia
*Assistant Examiner* — Kaipeen Yang
(74) *Attorney, Agent, or Firm* — Fox Rothschild LLP

(57) ABSTRACT

The present invention relates to a compound of formula (I) AA-AA-AA-X—Y—Z wherein, in any order, 2 of said AA (amino acid) moieties are cationic amino acids and 1 of said AA is an amino acid with a lipophilic R group, the R group having 14-27 non-hydrogen atoms; X is a N atom, which may be substituted by a branched or unbranched $C_1$-$C_{10}$ alkyl or aryl group which group may incorporate up to 2 heteroatoms selected from N, O and S; Y represents a group selected from —$R_a$—$R_b$—, —$R_a$—$R_b$—$R_b$— and —$R_b$—$R_b$—$R_a$— wherein $R_a$ is C, O, S or N, and $R_b$ is C; each of $R_a$ and $R_b$ may be substituted by $C_1$-$C_4$ alkyl groups or unsubstituted; and Z is a group comprising 1 to 3 cyclic groups each of 5 or 6 non-hydrogen atoms, 2 or more of the cyclic groups may be fused and one or more of the cyclic groups may be substituted; the Z moiety incorporates a maximum of 15 non-hydrogen atoms; and wherein the bond between Y and Z is a covalent bond between $R_a$ or $R_b$ of Y and a non-hydrogen atom of one of the cyclic groups of Z. The invention further relates to formulations containing these compounds and their uses in therapy, particularly as antimicrobial or antitumoural agents.

18 Claims, 4 Drawing Sheets

ANTIMICROBIAL COMPOUNDS

CROSS REFERENCE TO RELATED APPLICATIONS

This application is a 371 National Phase Application of PCT/GB08/04245 filed Dec. 20, 2008, which claims priority to GB Application No. 0724951.9 filed Dec. 20, 2007. Both applications are incorporated herein by reference.

The present invention relates to bioactive molecules, in particular to peptides which exhibit antimicrobial activity.

Peptides and their derivatives have long been recognised as therapeutically interesting molecules. A wide variety of organisms use peptides as part of their host defence mechanism. Antimicrobial peptides have been isolated from species as diverse as bacteria and mammals. Generally, these peptides have a net positive charge and a propensity to form amphiphilic α-helix or β-sheet structures upon interaction with the outer phospholipid bilayer in bacterial cell membranes. In most cases the detailed molecular mechanisms of the antibiotic action are unknown, although some peptides categorised as class L (lytic) peptides are believed to interact with bacterial cell membranes, probably forming ion-channels or pores.

The majority of known antibacterial peptides comprise 10 or more, typically 20 or more amino acids, this number of amino acid being required in order to provide sufficient length for the peptide, generally in α-helical form, to span the bacterial cell membrane and form a pore. Such a mechanism is the generally accepted way in which the majority of such peptides exert their cytotoxic activity.

Synthesis of the antibacterial peptides of the prior art can be difficult, and typically requires the peptides to be synthesised by bacteria or other organisms which can be cultured and harvested to yield the peptide of interest, additional processing steps after isolation of the direct product of translation are generally required. If active peptides could be identified which were shorter, this would enable economic manufacture by synthesis from the amino acid building blocks or available di- or tri-peptides. In addition, short peptides would offer advantages for biodelivery. There is a growing demand for antibiotics which can be administered without the need for an injection, such as by inhalation and absorption across the blood capillaries of the nasal passages.

The search for novel antibiotics has taken on particular urgency because of the increasing number of bacterial strains which are exhibiting resistance to known and extensively used drugs. Those operating in the fields of medicine as well as agriculture, environmental protection and food safety are constantly requiring new antibacterial agents and may have to treat a given population or site with several different antibacterial agents in order to effectively combat the undesirable bacteria.

As described in WO 01/66147, it has recently been shown that it is in fact possible to generate small antibiotic molecules, particularly peptides, which are believed to act through membrane destabilisation.

The present inventors have now identified a small group of modified peptides which exhibit an impressive set of characteristics, in particular a useful combination of antimicrobial activity, low toxicity and stability, i.e. resistance to enzymatic degradation.

Thus in one aspect is provided a compound, preferably a peptide, of formula (I)

AA-AA-AA-X—Y—Z  (I)

wherein, in any order, 2 of said AA (amino acid) moieties are cationic amino acids, preferably lysine or arginine but may be histidine or any non-genetically coded or modified amino acid carrying a positive charge at pH 7.0, and 1 of said AA is an amino acid with a large lipophilic R group, the R group having 14-27 non-hydrogen atoms and preferably containing 2 or more, e.g. 2 or 3, cyclic groups which may be fused or connected, these cyclic groups will typically comprise 5 or 6 non-hydrogen atoms, preferably 6 non-hydrogen atoms;

X is a N atom, which may be but preferably is not substituted by a branched or unbranched $C_1$-$C_{10}$ alkyl or aryl group, e.g. methyl, ethyl or phenyl, and this group may incorporate up to 2 heteroatoms selected from N, O and S;

Y represents a group selected from —$R_a$—$R_b$—, —$R_a$—$R_b$—$R_b$— and —$R_b$—$R_b$—$R_a$— wherein
$R_a$ is C, O, S or N, preferably C, and
$R_b$ is C; each of $R_a$ and $R_b$ may be substituted by $C_1$-$C_4$ alkyl groups or unsubstituted, preferably Y is —$R_a$—$R_b$— (in which $R_a$ is preferably C) and preferably this group is not substituted, when Y is —$R_a$—$R_b$—$R_b$— or $R_b$—$R_b$—$R_a$— then preferably one or more of $R_a$ and $R_b$ is substituted; and Z is a group comprising 1 to 3 cyclic groups each of 5 or 6 non-hydrogen atoms (preferably C atoms), 2 or more of the cyclic groups may be fused; one or more of the rings may be substituted and these substitutions may, but will typically not, include polar groups, suitable substituting groups include halogens, preferably bromine or fluorine and $C_1$-$C_4$ alkyl groups; the Z moiety incorporates a maximum of 15 non-hydrogen atoms, preferably 5-12, most preferably it is phenyl;

the bond between Y and Z is a covalent bond between $R_a$ or $R_b$ of Y and a non-hydrogen atom of one of the cyclic groups of Z.

Suitable non-genetically coded amino acids and modified amino acids which can provide a cationic amino acid include analogues of lysine, arginine and histidine such as homolysine, ornithine, diaminobutyric acid, diaminopimelic acid, diaminopropionic acid and homoarginine as well as trimethylysine and trimethylornithine, 4-aminopiperidine-4-carboxylic acid, 4-amino-1-carbamimidoylpiperidine-4-carboxylic acid and 4-guanidinophenylalanine.

The large lipophilic R group may contain hetero atoms such as O, N or S but typically there is no more than one heteroatom, preferably it is nitrogen. This R group will preferably have no more than 2 polar groups, more preferably none or one, most preferably none.

In a preferred embodiment the compounds, preferably peptides, of the invention are of formula (II)

$AA_1$-$AA_2$-$AA_1$-X—Y—Z  (II)

wherein:
$AA_1$ is a cationic amino acid, preferably lysine or arginine but may be histidine or any non-genetically coded or modified amino acid carrying a positive charge at pH 7.0;

$AA_2$ is an amino acid with a large lipophilic R group, the R group having 14-27 non-hydrogen atoms and preferably containing 2 or more, e.g. 2 or 3, cyclic groups which may be fused or connected, these cyclic groups will typically comprise 5 or 6 non-hydrogen atoms, preferably 6 non-hydrogen atoms; and X, Y and Z are as defined above.

Further compounds of the invention include compounds of formulae (III) and (IV):

$AA_2$-$AA_1$-$AA_1$-X—Y—Z  (III)

$AA_1$-$AA_1$-$AA_2$-X—Y—Z  (IV)

wherein $AA_1$, $AA_2$, X, Y and Z are as defined above. However molecules of formula (II) are preferred.

From amongst the above compounds certain are preferred. In particular, compounds wherein the amino acid with a large lipophilic R group, conveniently referred to herein as $AA_2$, is tributyl tryptophan (Tbt) or a biphenylalanine derivative such as Bip (4-(2-Naphthyl)), Bip (4-(1-Naphthyl)), Bip (4-n-Bu), Bip (4-Ph) or Bip (4-T-Bu); Bip (4-(2-Naphthyl)) and Tbt being most preferred. Another preferred group of compounds are those wherein Y is —$R_a$—$R_b$— as defined above, preferably wherein $R_a$ and $R_b$ are unsubstituted, most preferably wherein $R_a$ and $R_b$ are both carbon atoms.

A further preferred group of compounds are those in which —X—Y—Z together is the group —$NHCH_2CH_2Ph$.

The compounds include all enantiomeric forms, both D and L amino acids and enantiomers resulting from chiral centers within the amino acid R groups and moieties Y or Z.

Most preferred compounds are the following:

Compound 1

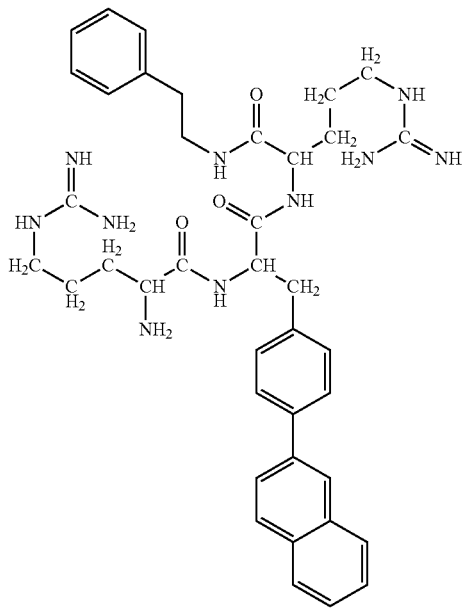

Compound 2

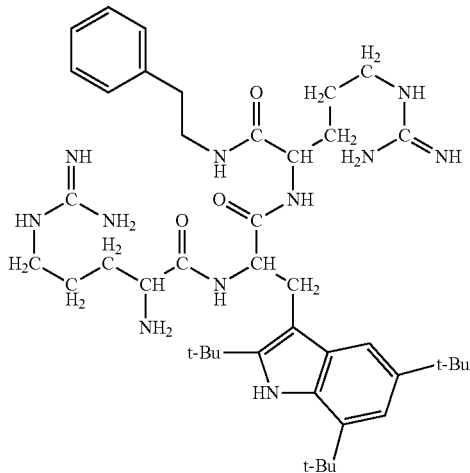

In a further aspect is provided compounds of formulae (I), (II), (III) or (IV) for use in therapy, particularly for use as an antimicrobial (e.g. antibacterial) agent but also as an antitumour agent. The molecules of the invention are also effective as antifungal agents and their uses as such and in methods of treating (including preventing) fungal infections constitute further aspects of the present invention. Onchyomycosis is particularly suited to treatment with molecules of the invention. Preferred molecules of the invention are active both as antifungal and antibacterial agents.

Such antimicrobial molecules also have non-therapeutic uses, for example in agriculture or in domestic or industrial situations as sterilising agents for materials susceptible to microbial contamination. Thus, in a further aspect, the present invention provides the use of the molecules of the invention as antimicrobial, particularly as antibacterial agents.

The molecules exhibit antimicrobial activity, in particular they exert a cytotoxic effect through a direct membrane-affecting mechanism and can be termed membrane acting antimicrobial agents. These molecules are lytic, destabilising or even perforating the cell membrane. This offers a distinct therapeutic advantage over agents which act on or intereact with proteinaceous components of the target cells, e.g. cell surface receptors. While mutations may result in new forms of the target proteins leading to antibiotic resistance, it is much less likely that radical changes to the lipid membranes could occur to prevent the cytotoxic effect. The lytic effect causes very rapid cell death and thus has the advantage of killing bacteria before they have a chance to multiply. In addition, the molecules may have other useful properties which kill or harm the target microbes e.g. an ability to inhibit protein synthesis, thus they may have multi-target activity.

Thus in a further aspect is provided the molecules of the invention for use in destabilising and/or permeabilising microbial cell membranes. By 'destabilising' is meant a perturbation of the normal three dimensional lipid bi-layer configuration including but not limited to membrane thinning, increased membrane permeability (typically not involving channels) to water, ions or metabolites etc. which also impairs the respiratory systems of the bacteria.

β and γ amino acids as well as α amino acids are included within the term 'amino acids', as are N-substituted glycines which may all be considered AA units. The molecules of the invention include beta peptides and depsipeptides.

The compounds of formulae (I) to (IV) may be peptidomimetics and peptidomimetics of the peptides described and defined herein are a further aspect of the present invention. A peptidomimetic is typically characterised by retaining the polarity, three dimensional size and functionality (bioactivity) of its peptide equivalent but wherein the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub provides a general discussion of techniques for the design and synthesis of peptidomimetics. In the present case, where the molecule is reacting with a membrane rather than the specific active site of an enzyme, some of the problems described of exactly mimicing affinity and efficacy or substrate function are not relevant and a peptidomimetic can be readily prepared based on a given peptide structure or a motif of required functional groups. Suitable amide bond surrogates include the following groups: N-alkylation (Schmidt, R. et al., Int. J. Peptide Protein Res., 1995, 46,47), retro-inverse amide (Chorev, M and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391).

The peptidomimetic compounds of the present invention may have 3 identifiable sub-units which are approximately equivalent in size and function to amino acids (AA units). The term 'amino acid' may thus conveniently be used herein to refer to the equivalent sub-units of a peptidomimetic compound. Moreover, peptidomimetics may have groups equivalent to the R groups of amino acids and discussion herein of suitable R groups and of N and C terminal modifying groups applies, mutatis mutandis, to peptidomimetic compounds.

As is discussed in the text book referenced above, as well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Peptidomimetics and thus peptidomimetic backbones wherein the amide bonds have been replaced as discussed above are, however, preferred.

Suitable peptidomimetics include reduced peptides where the amide bond has been reduced to a methylene, amine by treatment with a reducing agent e.g. borane or a hydride reagent such as lithium aluminium-hydride. Such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142. Strongly basic conditions will favour N-methylation over O-methylation and result in methylation of some or all of the nitrogen atoms in the peptide bonds and the N-terminal nitrogen.

Preferred peptidomimetic backbones include polyesters, polyamines and derivatives thereof as well as substituted alkanes and alkenes. The peptidomimetics will preferably have N and C terminii which may be modified as discussed herein.

The invention provides methods of treating microbial infections by administering the various molecules described herein. Likewise methods of destabilising microbial cell membranes are provided. The amount administered should be effective to kill all or a proportion of the target microbes or to prevent or reduce their rate of reproduction or otherwise to lessen their harmful effect on the body. The clinician or patient should observe improvement in one or more of the parameters or symptoms associated with the infection. Administration may also be prophylactic.

The peptides of the invention may be synthesised in any convenient way. Generally the reactive groups present (for example amino, thiol and/or carboxyl) will be protected during overall synthesis. The final step in the synthesis will thus be the deprotection of a protected derivative of the invention.

In building up the peptide, one can in principle start either at the C-terminal or the N-terminal although the C-terminal starting procedure is preferred.

Methods of peptide synthesis are well known in the art but for the present invention it may be particularly convenient to carry out the synthesis on a solid phase support, such supports being well known in the art.

A wide choice of protecting groups for amino acids are known and suitable amine protecting groups may include carbobenzoxy (also designated Z) t-butoxycarbonyl (also designated Boc), 4-methoxy-2,3,6-trimethylbenzene sulphonyl (Mtr) and 9-fluorenylmethoxy-carbonyl (also designated Fmoc). It will be appreciated that when the peptide is built up from the C-terminal end, an amine-protecting group will be present on the α-amino group of each new residue added and will need to be removed selectively prior to the next coupling step.

Carboxyl protecting groups which may, for example be employed include readily cleaved ester groups such as benzyl (Bzl), p-nitrobenzyl (ONb), pentachlorophenyl (OPClP), pentafluorophenyl (OPfp) or t-butyl (OtBu) groups as well as the coupling groups on solid supports, for example methyl groups linked to polystyrene.

Thiol protecting groups include p-methoxybenzyl (Mob), trityl (Trt) and acetamidomethyl (Acm).

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoroacetic acid. Thiol protecting groups such as Trt may be removed selectively using an oxidation agent such as iodine.

References and techniques for synthesising peptidomimetic compounds and the other bioactive molecules of the invention are described herein and thus are well known in the art.

Formulations comprising one or more compounds of the invention in admixture with a suitable diluent, carrier or excipient constitute a further aspect of the present invention. Such formulations may be for, inter alia, pharmaceutical (including veterinary) or agricultural purposes or for use as sterilising agents for materials susceptible to microbial contamination, e.g. in the food industry. Suitable diluents, excipients and carriers are known to the skilled man.

The peptides defined herein exhibit broad antimicrobial activity and thus are also suitable as antiviral and antifungal agents, which will have pharmaceutical and agricultural applications, and as promoters of wound healing or spermicides. All of these uses constitute further aspects of the invention.

Methods of treating or preventing bacterial, viral or fungal infections or of treating tumours which comprises administration to a human or animal patient one or more of the peptides or peptidomimetics as defined herein constitute further aspects of the present invention.

The compositions according to the invention may be presented, for example, in a form suitable for oral, nasal, parenteral, intravenal, intratumoral or rectal administration.

As used herein, the term "pharmaceutical" includes veterinary applications of the invention.

The active compounds defined herein may be presented in the conventional pharmacological forms of administration, such as tablets, coated tablets, nasal sprays, solutions, emulsions, liposomes, powders, capsules or sustained release forms.

The peptides are particularly suitable for topical administration, e.g. in the treatment of diabetic ulcers or fungal infections such as onchyomycosis. Formulations for topical administration are preferably in the form of a gel, cream, lotion, paste or other preparation which is more viscous than water. Further formulations for topical application include dressings, gauzes etc. which have been impregnated with a compound of the invention; when impregnating such materials the preparation containing a compound of the invention need not be more viscous than water. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays which are a preferred method of administration may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the active molecules preferably contain 0.1-10 mg, for example 1-5 mg of the antimicrobial agent. The pharmaceutical compositions may additionally comprise further active ingredients, including other cytotoxic agents such as other antimicrobial peptides. Other active ingredients may include different types of antibiotics, cytokines e.g. IFN-γ, TNF, CSF and growth factors, immunomodulators, chemotherapeutics e.g. cisplatin or antibodies.

The bioactive molecules, when used in topical compositions, are generally present in an amount of at least 0.1%, by weight. In most cases, it is not necessary to employ the peptide in an amount greater than 1.0%, by weight.

In employing such compositions systemically (intramuscular, intravenous, intraperitoneal), the active molecule is present in an amount to achieve a serum level of the bioactive molecule of at least about 5 ug/ml. In general, the serum level need not exceed 500 ug/ml. A preferred serum level is about 100 ug/ml. Such serum levels may be achieved by incorporating the bioactive molecule in a composition to be administered systemically at a dose of from 1 to about 10 mg/kg. In general, the molecule(s) need not be administered at a dose exceeding 100 mg/kg.

Methods of treating environmental or agricultural sites or products, as well as foodstuffs and sites of food production, or surfaces or tools e.g. in a hospital environment with one or more of the molecules of the invention to reduce the numbers of viable bacteria present or limit bacterial growth or reproduction constitute further aspects of the present invention.

The invention will now be further described with reference to the following non-limiting Examples and Figures, in which FIG. 1 is a graph showing the effect of one day topical treatment using compound 2 against *Staphylococcus aureus* FDA486 in a murine skin infection model. The number of colony forming units (CFU) are shown on the Y-axis and the type of topical treatment applied to the mice is shown on the X-axis.

EXAMPLES

Example 1

Figure 1:
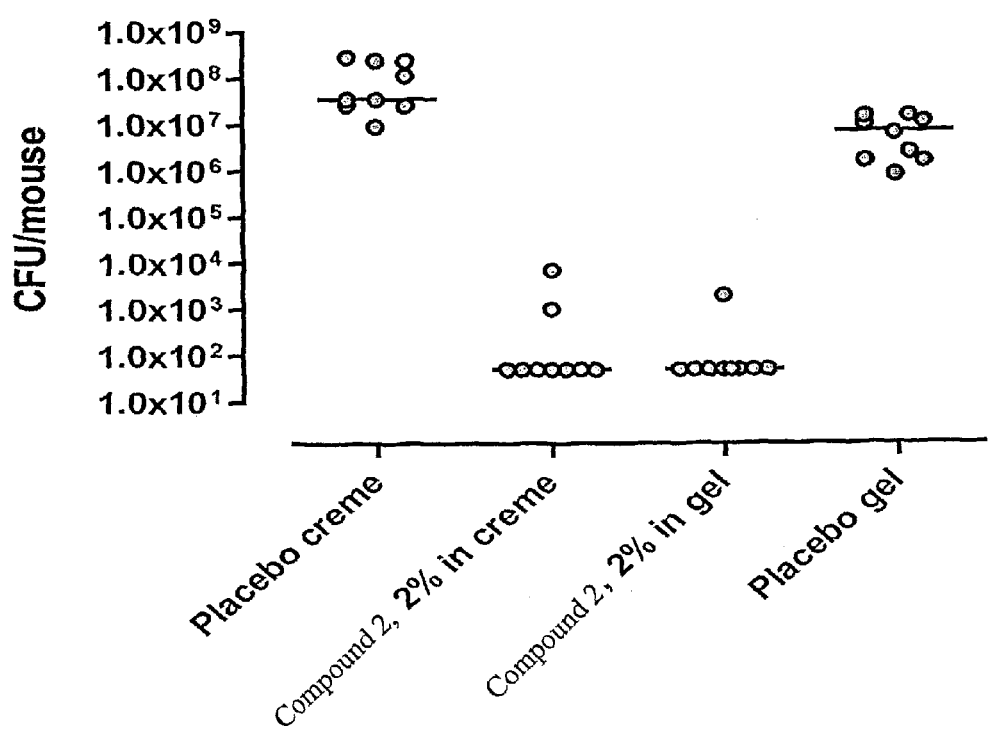

In Vitro Activities of the Molecules of the Invention
2.0 Materials and Methods
2.1 Antimicrobials
Vials of pre-weighed Compound 1 and Compound 2 were supplied by Lytix Biopharma AS.

| General compound formula: $AA_1$-$AA_2$-$AA_1$-XYZ | | | |
|---|---|---|---|
| | $AA_1$ | $AA_2$ | XYZ |
| Compound 1 | Arg | Phe(4-(2-Naphtyl)) | $NHCH_2CH_2Ph$ |
| Compound 2 | Arg | 2,5,7-tri-tert-butyltryptophan | $NHCH_2CH_2Ph$ |

2.2 Bacterial Isolates

Bacterial isolates used in this study were from various sources worldwide stored at GR Micro Ltd. and maintained, with minimal sub-culture, deep frozen at −70° C. as a dense suspension in a high protein matrix of undiluted horse serum. The species used and their characteristics are listed in Table 1. These included 54 Gram-positive bacteria, 33 Gram-negative bacteria and 10 fungi.

2.3 Determination of Minimum Inhibitory Concentration (MIC)

MICS were determined using the following microbroth dilution methods for antimicrobial susceptibility testing published by the Clinical and Laboratory Standards Institute (CLSI, formerly NCCLS):

M7-A6 Vol. 23 No. 2 January 2003 Methods for Dilution Antimicrobial Susceptibility Tests for Bacteria that Grow Aerobically; Approved Standard-Sixth Edition.

M100-S15 Vol. 25 No 1. January 2005 Performance Standards for Antimicrobial Susceptibility Testing; Fifteenth Informational Supplement.

M11-A6 Vol. 24 No. 2 Methods for Antimicrobial Susceptibility Testing of Anaerobic Bacteria; Approved Standard-Sixth Edition.

M27-A2 Vol. 22 No. 15 Reference Method for Broth Dilution Antifungal Susceptibility Testing of Yeasts; Approved Standard-Second Edition.

M38-A Vol. 22 No. 16 Reference Method for Broth Dilution Antifungal Susceptibility Testing of Filamentous Fungi; Approved Standard.

MIC estimations were performed using wet plates, containing the antibacterials or antifungals, prepared at GR Micro Ltd.

Cation-adjusted Mueller-Hinton broth (Oxoid Ltd., Basingstoke, UK and Trek Diagnostic Systems Ltd., East Grinstead, UK) (supplemented with 5% laked horse blood for *Streptococcus* spp., *Corynebacterium jeikeium* and *Listeria monocytogenes*) was used for aerobic bacteria, with an initial inoculum of approximately $10^5$ colony-forming units (CFU)/mL.

*Haemophilus* test medium (Mueller-Hinton broth containing 0.5% yeast extract and *Haemophilus* test medium supplement which contains 15 mg/L of each of haematin and NAD, all obtained from Oxoid Ltd., Basingstoke, UK) was used for the *Haemophilus influenzae* and inoculated with approximately $10^5$ CFU/mL.

Supplemented *Brucella* broth (SBB) was used for the anaerobic strains with an inoculum of approximately $10^6$ CFU/mL. SBB is a broth consisting of 1% peptone, 0.5% 'Lab-lemco', 1% glucose and 0.5% sodium chloride supplemented with 5 µg/L haemin and 1 µg/L vitamin K (both obtained from Sigma Aldrich Ltd.)

Yeast and filamentous fungal MIC were performed in MOPS buffered RPMI 1640 medium (MOPS buffer obtained from Sigma Aldrich Ltd., RPMI 1640 obtained from Invitrogen Ltd, Paisley, Scotland). The yeast inocula were in the range $7.5 \times 10^2$-$4 \times 10^3$ CFU/mL and the filamentous fungi approximately $8 \times 10^3$-$1 \times 10^5$ CFU/mL Following normal practice all the plates containing Mueller-Hinton broth were prepared in advance, frozen at $-70°$ C. on the day of preparation and defrosted on the day of use. Fungal, *Haemophilus* and anaerobic MIC determinations were all performed in plates prepared on the same day.

To evaluate whether freezing affected the activity of the peptides some MIC determinations were repeated using plates containing freshly-prepared Mueller-Hinton broth.

2.4 Control Strains

The following control (reference) strains were included in the panel of strains tested

| | |
|---|---|
| *Escherichia coli* | ATCC 25922 |
| *Staphylococcus aureus* | ATCC 29213 |
| *Enterococcus faecalis* | ATCC 29212 |
| *Streptococcus pneumoniae* | ATCC 49619 |
| *Pseudomonas aeruginosa* | ATCC 27853 |
| *Candida krusei* | ATCC 6258 |

The control strains below were extra to the test strain panel and were included where appropriate, to check that the comparators were within range.

| | |
|---|---|
| *Haemophilus influenzae* | ATCC 49247 |
| *Candida parapsilosis* | ATCC 22019 |
| *Bacteroides fragilis* | ATCC 25285 |
| *Eggerthella lenta* | ATCC 43055 |

3.0 Results

The results are shown in Table 1 as a single line listing. Repeat control strain results are shown in Table. 2. It can be seen that the control strain results were highly reproducible including data from plates that contained Mueller Hinton broth either stored frozen or used fresh. Freezing plates also had no effect on the MIC for other bacterial strains.

The MIC data obtained is very encouraging and indicates that the peptides have quite a broad spectrum of activity.

TABLE 1

Single line list of the in vitro activity of two novel antimicrobial peptides and a comparator against a panel of Gram-positive bacteria, Gram-negative bacteria and fungi.

| Species and properties | Compound 1 | Compound 2 |
|---|---|---|
| *Candida albicans* ATCC90028 - reference strain | 2 | 8 |
| *Candida albicans* ATCC24433 - reference strain | 2 | 8 |
| *Candida tropicalis* ATCC750 - reference strain | 2 | 4 |
| *Candida parapsilosis* ATCC90018 - reference strain | 4 | 16 |
| *Candida (Issatchenkia) krusei* ATCC6258 - reference strain | 4 | 4 |
| *Aspergillus niger* - G.R. Micro collection | 4 | 8 |
| *Trichophyton mentagrophytes* - G.R. Micro collection | 16 | 8 |
| *Trichophyton interdigitale* - G.R. Micro collection | 8 | 8 |
| *Microsporum canis* - G.R. Micro collection | 8 | 8 |
| *Cryptococcus neoformans* - G.R. Micro collection | 4 | 4 |
| *Escherichia coli* ATCC25922 - antibiotic-susceptible type strain | 32 | 8 |
| *Escherichia coli* ATCC32518 - β-lactamase positive type strain | 32 | 8 |
| *Escherichia coli* - multi-drug resistant clinical isolate | 32 | 8 |
| *Klebsiella aerogenes* NCTC11228 - antibiotic-susceptible type strain | 32 | 16 |
| *Klebsiella aerogenes* - multi-drug resistant clinical isolate | 64 | 16 |
| *Enterobacter* sp - antibiotic-susceptible clinical isolate | 32 | 4 |
| *Enterobacter* sp - multi-drug resistant clinical isolate | 64 | 16 |
| *Pseudomonas aeruginosa* ATCC27853 - antibiotic-susceptible type | 16 | 8 |
| *Pseudomonas aeruginosa* - multi-drug resistant clinical isolate | 32 | 4 |
| *Stenotrophomonas maltophilia* - antibiotic-susceptible clinical isolate | 64 | 8 |
| *Salmonella* sp - antibiotic-susceptible clinical isolate | 16 | 8 |
| *Salmonella* sp - multi-drug resistant clinical isolate | 16 | 8 |

TABLE 1-continued

Single line list of the in vitro activity of two novel antimicrobial peptides and a comparator against a panel of Gram-positive bacteria, Gram-negative bacteria and fungi.

| Species and properties | Compound 1 | Compound 2 |
|---|---|---|
| *Shigella* sp - antibiotic-susceptible clinical isolate | 32 | 8 |
| *Morganella morganii* - multi-drug resistant clinical isolate | ≥128 | 16 |
| *Haemophilus influenzae* - β-lactamase negative clinical isolate | ≥128 | 8 |
| *Haemophilus influenzae* - β-lactamase positive clinical isolate | ≥128 | 8 |
| *Haemophilus influenzae* β-lactamase negative ampicillin-resistant | ≥128 | 8 |
| *Moraxella catarrhalis* - β-lactamase positive clinical isolate | 4 | 4 |
| *Moraxella catarrhalis* - reduced fluoroquinolone susceptibility clinical | 8 | 8 |
| *Acinetobacter baumanii* - antibiotic-susceptible clinical isolate | 64 | 16 |
| *Staphylococcus aureus* ATCC 29213 - antibiotic-susceptible control | 4 | 2 |
| *Staphylococcus aureus* ATCC 25923 - antibiotic-susceptible control | 4 | 4 |
| *Staphylococcus aureus* ATCC 43300 - methicillin-resistant control strain | 4 | 2 |
| *Staphylococcus aureus* - methicillin-resistant clinical isolate | 4 | 4 |
| *Staphylococcus aureus* - multi-drug-resistant clinical isolate | 8 | 4 |
| *Staphylococcus aureus* - teicoplanin-intermediate clinical isolate | 4 | 4 |
| *Staphylococcus epidermidis* antibiotic susceptible clinical isolate | 16 | 8 |
| *Staphylococcus epidermidis* methicillin-resistant clinical isolate | 2 | 4 |
| *Staphylococcus haemolyticus* - antibiotic susceptible clinical isolate | 4 | 4 |
| *Staphylococcus saprophyticus* - antibiotic susceptible clinical isolate | 1 | 1 |
| *Enterococcus faecalis* - ATCC 29212 antibiotic-susceptible control | 4 | 4 |
| *Enterococcus faecalis* vancomycin-susceptible clinical isolate | 8 | 8 |
| *Enterococcus faecalis* vancomycin-resistant (VanA) clinical isolate | 16 | 8 |
| *Enterococcus faecalis* vancomycin-resistant (VanB) clinical isolate | 16 | 16 |
| *Enterococcus faecalis* high-level gentamicin-resistant clinical isolate | 16 | 8 |
| *Enterococcus faecium* vancomycin-susceptible clinical isolate | 8 | 8 |
| *Enterococcus faecium* vancomycin-resistant (VanA) clinical isolate | 16 | 8 |
| *Enterococcus faecium* vancomycin-resistant (VanB) clinical isolate | 8 | 4 |
| *Enterococcus gallinarum* vancomycin-resistant (VanC) clinical isolate | 4 | 4 |
| *Streptococcus pneumoniae* - ATCC 49619 antibiotic-susceptible control | 32 | 16 |
| *Streptococcus pneumoniae* - penicillin-susceptible clinical isolate | 64 | 32 |
| *Streptococcus pneumoniae* -penicillin-intermediate clinical isolate | 32 | 32 |
| *Streptococcus pneumoniae* - penicillin-resistant clinical isolate | 32 | 16 |
| *Streptococcus pneumoniae* - multi-drug resistant clinical isolate | 64 | 32 |
| *Streptococcus pyogenes* - Macrolide (MLS) resistant clinical isolate | 32 | 16 |
| *Streptococcus pyogenes* - Macrolide (M-type) resistance clinical isolate | 32 | 16 |
| *Corynebacterium jeikeium* - antibiotic-susceptible clinical isolate | 32 | 16 |
| *Corynebacterium jeikeium* - multi-drug resistant clinical isolate | 32 | 8 |
| *Listeria monocytogenes* - antibiotic-susceptible clinical isolate | 32 | 16 |
| MU50 *Staphylococcus aureus* (MRSA) - VISA type strain | 4 | 4 |
| EMRSA3 *Staphylococcus aureus* (MRSA) - SSCmec type 1 | 4 | 4 |
| EMRSA16 *Staphylococcus aureus* (MRSA) - SSCmec type 2 | 4 | 4 |
| EMRSA1 *Staphylococcus aureus* (MRSA) - SSCmec type 3 | 8 | 8 |
| EMRSA15 *Staphylococcus aureus* (MRSA) - SSCmec type 4 | 4 | 4 |
| HT2001254 *Staphylococcus aureus* (MRSA) - PVL positive | 4 | 4 |
| *Streptococcus agalactiae* - antibiotic-susceptible clinical isolate | 16 | 8 |
| *Streptococcus agalactiae* - macrolide-resistant clinical isolate | 32 | 16 |
| Group C *Streptococcus* - antibiotic-susceptible clinical isolate | 32 | 16 |
| Group C *Streptococcus* - macrolide-resistant clinical isolate | 64 | 32 |
| Group G *Streptococcus* - antibiotic-susceptible clinical isolate | 32 | 8 |
| Group G *Streptococcus* - macrolide-resistant clinical isolate | 32 | 16 |
| *Streptococcus mitis* - antibiotic-susceptible clinical isolate | 64 | 16 |
| *Streptococcus mitis* - macrolide-resistant clinical isolate | ≥128 | 32 |
| *Streptococcus constellatus* - antibiotic-susceptible clinical isolate | 64 | 32 |
| *Streptococcus constellatus* - macrolide-resistant clinical isolate | 64 | 32 |
| *Streptococcus oralis* - antibiotic-susceptible clinical isolate | 64 | 32 |
| *Streptococcus oralis* - macrolide-resistant clinical isolate | 32 | 32 |
| *Streptococcus bovis* - antibiotic-susceptible clinical isolate | 64 | 32 |
| *Streptococcus bovis* - macrolide-resistant clinical isolate | 8 | 8 |
| *Streptococcus sanguis* - antibiotic-susceptible clinical isolate | 64 | 32 |
| *Streptococcus sanguis* - macrolide-resistant clinical isolate | 32 | 32 |
| *Clostridium perfringens* - antibiotic-susceptible clinical isolate | ≥128 | 32 |
| *Clostridium difficile* - antibiotic-susceptible clinical isolate | 32 | 16 |

TABLE 2

In vitro activity of two novel antimicrobial peptides and comparators against ATCC control strains (Including ATCC control strains extra to the test strain panel)

| Strain No. | Species and properties | Compound 1 | Compound 2 | Plate type |
|---|---|---|---|---|
| GP01 | *Staphylococcus aureus* ATCC 29213 antibiotic-susceptible control strain | 8 | 4 | Frozen MHB |
| GP01 | *Staphylococcus aureus* ATCC 29213 antibiotic-susceptible control strain | 4 | 4 | Frozen MHB |
| GP01 | *Staphylococcus aureus* ATCC 29213 antibiotic-susceptible control strain | 4 | 2 | Fresh MHB |
| GN01 | *Escherichia coli* ATCC 25922 antibiotic-susceptible type strain | 32 | 8 | Frozen MHB |
| GN01 | *Escherichia coli* ATCC 25922 antibiotic-susceptible type strain | 32 | 8 | Frozen MHB |
| GN01 | *Escherichia coli* ATCC 25922 antibiotic-susceptible type strain | 16 | 8 | Fresh MHB |
| GN10 | *Pseudomonas aeruginosa* ATCC 27853 antibiotic-susceptible type strain | 16 | 8 | Frozen MHB |
| GN10 | *Pseudomonas aeruginosa* ATCC 27853 antibiotic-susceptible type strain | 32 | 8 | Frozen MHB |
| GN10 | *Pseudomonas aeruginosa* ATCC 27853 antibiotic-susceptible type strain | 8 | 8 | Fresh MHB |
| GP11 | *Enterococcus faecalis* - ATCC 29212 antibiotic-susceptible control strain | 8 | 8 | Frozen MHB |
| GP11 | *Enterococcus faecalis* - ATCC 29212 antibiotic-susceptible control strain | 8 | 8 | Frozen MHB |
| GP11 | *Enterococcus faecalis* - ATCC 29212 antibiotic-susceptible control strain | 4 | 4 | Fresh MHB |
|  | *Haemophilus influenzae* - ATCC 47247 | 32 | 4 | HTM |
|  | *Candida parapsilosis* ATCC 22019 | 4 | 8 | RPMI 1640 |
| F05 | *Candida (Issatchenkia) krusei* ATCC 6258 reference strain | 8 | 8 | RPMI 1640 |
| F05 | *Candida (Issatchenkia) krusei* ATCC 6258 reference strain | 8 | 8 | RPMI 1640 |
|  | *Bacteroides fragilis* - ATCC 25285 | 64 | 64 | SBB |
|  | *Eggerthella lenta* - ATCC 43055 | 16 | 32 | SBB |

MHB, Mueller Hinton broth; HTM, *haemophilus* test medium; SBB, supplemented *Brucella* broth.

Example 2

Peptide Synthesis
Chemicals

Protected amino acids Boc-Trp-OH, Boc-Arg-OH, Boc-4-phenyl-Phe and Ac-Arg-OH were purchased from Bachem AG while Boc-4-iodophenylalanine, Boc-3,3-diphenylalanine and Boc-(9-anthryl)alanine were purchased from Aldrich. Benzylamine, 2-phenylethylamine, 3-phenylpropylamine, (R)-2-phenylpropylamine, (S)-2-phenylpropylamine, N,N-methylbenzylamine, N,N-ethylbenzylamine and N,N-dibenzylamine making up the C-terminal of the peptide were purchased from Fluka except N-ethylbenzylamine which was purchased from Acros. Diisopropylethylamine (DIPEA), 1-hydroxybenzotriazole (1-HOBt), chlorotripyrrolidinophosphonium hexafluorophosphate (PyCloP) and O-(benzotriazol-1-yl)-N,N,N',N'tetramethyluronium hexafluorophosphate (HBTU) were purchased from Fluka. 4-n-Butylphenylboronic acid, 4-t-butylphenylboronic acid, 4-biphenylboronic acid, 2-napthylboronic acid, tri ortho-tolylphosphine, benzylbromide and palladium acetate were purchased from Aldrich. Solvents were purchased from Merck, Riedel-de Haën or Aldrich.

Preparation of Amino Acids

Preparation of Boc-2,5,7-tri-tert-butyltryptophan-OH: A mixture of H2N-Trp-OH (1.8 g, 8.8 mmol), t-BuOH (4.7 g, 63.4 mmol) in trifluoroacetic acid (19 mL) is stirred at 70 OC for 3 hours. The volume of the resulting mid-brown translucent solution is reduced on a rotary evaporator at room temperature for 30 min and then triturated by means of adding 60 mL of 7% (by weight) NaHCO3 drop-wise. The gray/white granular solid obtained is then recovered by vacuum filtration and dried in vacuo at room temperature for 24 hours. The product is isolated by crystallization from a near boiling mixture of 40% ethanol in water. Volumes typically are approximately 20 mL per gram of crude product.

A first crystallization from crude produces isolated product of 80-83% purity (HPLC) with respect to all other substances in the sample and approximately 94-95% purity with respect to the known TBT analogues. Yields at this stage are in the range 60-65%.

Benzylation of Boc-4-iodophenylalanine.

Boc-4-iodophenylalanine (1 equivalent) was dissolved in 90% methanol in water and neutralized by addition of cesium carbonate until a weak alkaline pH (determined by litmus paper). The solvent was removed by rotary evaporation, and remaining water in the cesium salt of Boc-4-iodophenylalanine was further reduced by repeated azeotropic distillation with toluene. The resulting dry salt was dissolved in dimethylformamide (DMF), benzylbromide (1.2 equivalents) was added and the resulting mixture was stirred for 6-8 h. At the end of the reaction DMF was removed under reduced pressure and an oil containing the title compound is formed. This oil was dissolved in ethyl acetate and the resulting solution was washed with equal volumes of citric acid solution (three times), sodium bicarbonate solution and brine. The title compound was isolated as a pale yellow oil in 85% yield by flash chromatography using dichloromethane:ethyl acetate (95:5) as eluent. Crystalline benzyl Boc-4-iodophenylalanine could be obtained by recrystallisation from n-heptane.

General Procedure for Suzuki Couplings:

Benzyl Boc-4-iodophenylalanine (1 equivalent), arylboronic acid (1.5 equivalents), sodium carbonate (2 equivalents), palladium acetate (0.05 equivalent) and tri orthotolylphosphine (0.1 equivalent) was added to a degassed mixture of dimethoxyethane (6 ml/mmol benzyl Boc-4-iodophenylalanine) and water (1 ml/mmol benzyl Boc-4-iodophenylalanine). The reaction mixture was kept under argon and heated to 80° C. for 4-6 h. After cooling to room temperature the mixture is filtered through a short pad of silicagel and sodium carbonate. The filter cake was further washed with ethyl acetate. The filtrates were combined and the solvents were removed under reduced pressure. The products were isolated by flash chromatography using mixtures of ethyl acetate and n-hexane as eluent.

Preparation of Boc-Bip(n-Bu)-OBn:

The title compound was prepared in 53% yield from 4-n-butylphenylboronic acid using the general procedure for Suzuki couplings. Boc-Bip(n-Bu)-OBn was isolated using an 80:20 ethyl acetate:n-hexane eluent.

Preparation of Boc-Bip(t-Bu)-OBn:

The title compound was prepared in 79% yield from 4-t-butylphenylboronic acid using the general procedure for Suzuki couplings. Boc-Bip(t-Bu)-OBn was isolated using an 80:20 ethyl acetate:n-hexane eluent.

Preparation of Boc-Bip(4-Ph)-OBn:

The title compound was prepared in 61% yield from 4-biphenylboronic acid using the general procedure for Suzuki couplings. Boc-Bip(4-Ph)-OBn was isolated by recrystallisation of the crude product from n-heptane.

Preparation of Boc-Bip(4-(2-Naphtyl))-OBn:

The title compound was prepared in 68% yield from 2-naphtylboronic acid using the general procedure for Suzuki couplings. Boc-Bip(4-(2-Naphtyl))-OBn was isolated by recrystallisation of the crude product from n-heptane.

Preparation of Boc-Bip(4-(1-Naphtyl))-OBn:

The title compound was prepared from 2-naphtylboronic acid using the general procedure for Suzuki couplings. Boc-Bip(4-(1-Naphtyl))-OBn was isolated by recrystallisation of the crude product from n-heptane.

General Procedure for Deesterification of Benzyl Esters:

The Benzyl ester is dissolved in DMF and hydrogenated for 2 days at ambient pressure using 10% Pd on carbon as catalyst. At the end of the reaction the catalyst is removed by filtration and the solvent is removed under reduced pressure. The free acids are isolated by recrystallisation from diethyl ether.

Preparation of Boc-Bip(4-n-Bu)-OH:

The title compound was prepared in 61% yield from Boc-Bip(n-Bu)-OBn using the general procedure for deesterification.

Preparation of Boc-Bip(4-t-Bu)-OH:

The title compound was prepared in 65% yield from Boc-Bip(t-Bu)-OBn using the general procedure for deesterification.

Preparation of Boc-Bip(4-Ph)-OH:

The title compound was prepared in 61% yield from Boc-Bip(4-ph)-OBn using the general procedure for deesterification.

Preparation of Boc-Bip(4-(2-Naphtyl))-OH:

The title compound was prepared in 68% yield from Boc-Bip(4-(2-Naphtyl))-OBn using the general procedure for deesterification.

Preparation of Boc-Bip(4-(2-Naphtyl))-OH:

The title compound was prepared in 68% yield from Boc-Bip(4-(2-Naphtyl))-OBn using the general procedure for deesterification.

General Procedure for Solution Phase Peptide Synthesis Using HBTU.

The peptides were prepared in solution by stepwise amino acid coupling using Boc protecting strategy according to the following general procedure. The C-terminal peptide part with a free amino group (1 eq) and the Boc protected amino acid (1.05 eq) and 1-hydroxybenzotriazole (1-HOBt) (1.8 eq) were dissolved in DMF (2-4 ml/mmol amino component) before addition of diisopropylethylamine (DIPEA) (4.8 eq). The mixture was cooled on ice and O-(benzotriazol-1-yl)-N,N,N',N'tetramethyluronium hexafluorophosphate (HBTU) (1.2 eq) was added. The reaction mixture was shaken at ambient temperature for 1-2 h. The reaction mixture was diluted by ethyl acetate and washed with citric acid, sodium bicarbonate and brine. The solvent was removed under vacuum and the Boc protecting group of the resulting peptide was deprotected in the dark using 95% TFA or acetylchloride in anhydrous methanol.

Solution Phase Amide Formation Using PyCloP.

Synthesis of Boc-Arg-N($CH_2Ph)_2$. A solution of Boc-Arg-OH(1 eq), NH($CH_2Ph)_2$ (1.1 eq) and PyCloP (1 eq) in dry DCM (filtered through alumina) (2 ml) and DMF (1 ml). The solution was cooled on ice and DIPEA (2 eq) was added under stirring. The solution was stirred for 1 h at room temperature. The reaction mixture was evaporated, and redissolved in ethyl acetate and washed with citric acid, sodium bicarbonate and brine. The solvent was removed under vacuum and the Boc protecting group of the resulting peptide was deprotected in the dark using 95% TFA.

Peptide Purification and Analysis.

The peptides were purified using reversed phase HPLC on a Delta-Pak (Waters) $C_{18}$ column (100 Å, 15 μm, 25×100 mm) with a mixture of water and acetonitrile (both containing 0.1% TFA) as eluent. The peptides were analyzed by RP-HPLC using an analytical Delta-Pak (Waters) $C_{18}$ column (100 Å, 5 μm, 3.9×150 mm) and positive ion electrospray mass spectrometry on a VG Quattro quadrupole mass spectrometer (VG Instruments Inc., Altringham, UK).

Example 3

Stability Towards Tryptic Degration

Compounds of formula $AA_1$-$AA_2$-$AA_1$-$NHCH_2CH_2Ph$ were tested for their trypsin resistance and antimicrobial activity.

Measurements and Calculation of Peptide Half-Life

Each peptide was dissolved in a 0.1 M $NH_4HCO_3$ buffer (pH 6.5) to yield a final peptide concentration of 1 mg/ml. A trypsin solution was prepared by dissolving 1 mg of trypsin in 50 ml 0.1 M $NH_4HCO_3$ buffer (pH 8.2). For the stability determination, 250 μl freshly made trypsin solution and 250 μl peptide solution were incubated in 2 ml of 0.1 M $NH_4HCO_3$ buffer (pH 8.6) at 37° C. on a rocking table. Aliquots of 0.5 ml were sampled at different time intervals, diluted with 0.5 ml water:acetonitrile (60:40 v/v) containing 1% TFA and analysed by RP-HPLC as described above. Samples without trypsin addition taken at 0 h and after 20 h at 37° C. were used as negative controls. Integration of the peak area at 254 nm for samples taken during the first 5 hours of the assay was used to generate the $\tau_{1/2}$. Peptides that displayed no degradation during the first 24 h were classified as stable.

Antibacterial Assay

MIC determinations on *Staphylococcus aureus*, strain ATCC 25923, Methicillin resistant *Staphylococcus aureus* (MRSA) strain ATCC 33591 and Methicillin resistant *Staphylococcus epidermidis* (MRSE) strain ATCC 27626 were performed by Toslab AS using standard methods. Amsterdam, D. (1996) Susceptibility testing of antimicrobials in liquid media, in *Antibiotics in Laboratory Medicine*. 4th ed (Lorian, V., Ed.) pp 75-78, Williams and Wilkins Co, Baltimore.

available Loceryl® in MedPharm's in vitro TCCTTM infected nail model using human nails.

Materials

Test item 1 is Compound 2 as a HCl salt. Reference item 1 is Loceryl® Nail Lacquer

TABLE 3

Stability of $AA_1$-$AA_2$-$AA_1$-$NHCH_2CH_2Ph$ peptides towards trypsin measured as half-life ($\tau_{1/2}$) and antibacterial activities displayed as MIC.

| Peptide | $AA_1$ | $AA_2$ | $\tau_{1/2}{}^a$ (h) | $MIC^b$ ($\mu M$) | | |
|---|---|---|---|---|---|---|
| | | | | *S. aureus*$^c$ | MRSA$^d$ | MRSE$^e$ |
| Compound 6$^f$ | Arg | Trp | 7 | 145 | 97 | 81 |
| Compound 5 | Arg | Bip(4-Ph) | Stable | 5 | 3 | 3 |
| Compound 4 | Lys | 2,5,7-tri-tert-butyltryptophan | Stable | | 3 | <2 |
| Compound 3 | Arg | Phe(4-(1-Naphtyl)) | 20 | | 3 | 3 |
| Compound 2 | Arg | 2,5,7-tri-tert-butyltryptophan | Stable | <3 | <3 | <3 |
| Compound 1 | Arg | Phe(4-(2-Naphtyl)) | Stable | 4 | <3 | <3 |

$^a$Medical Calculator from Cornell University was used to calculate the half-life.
$^b$Minimal inhibitory concentration
$^c$*Staphylococcus aures* strain ATCC 25923
$^d$Methicillin resistant *Staphylococcus aureus* ATCC 33591
$^e$Methicillin resistant *Staphylococcus epidermis* ATCC 27626
$^f$not within scope of invention

Example 4

In Vivo Activity of Compound 2

Figure 2:
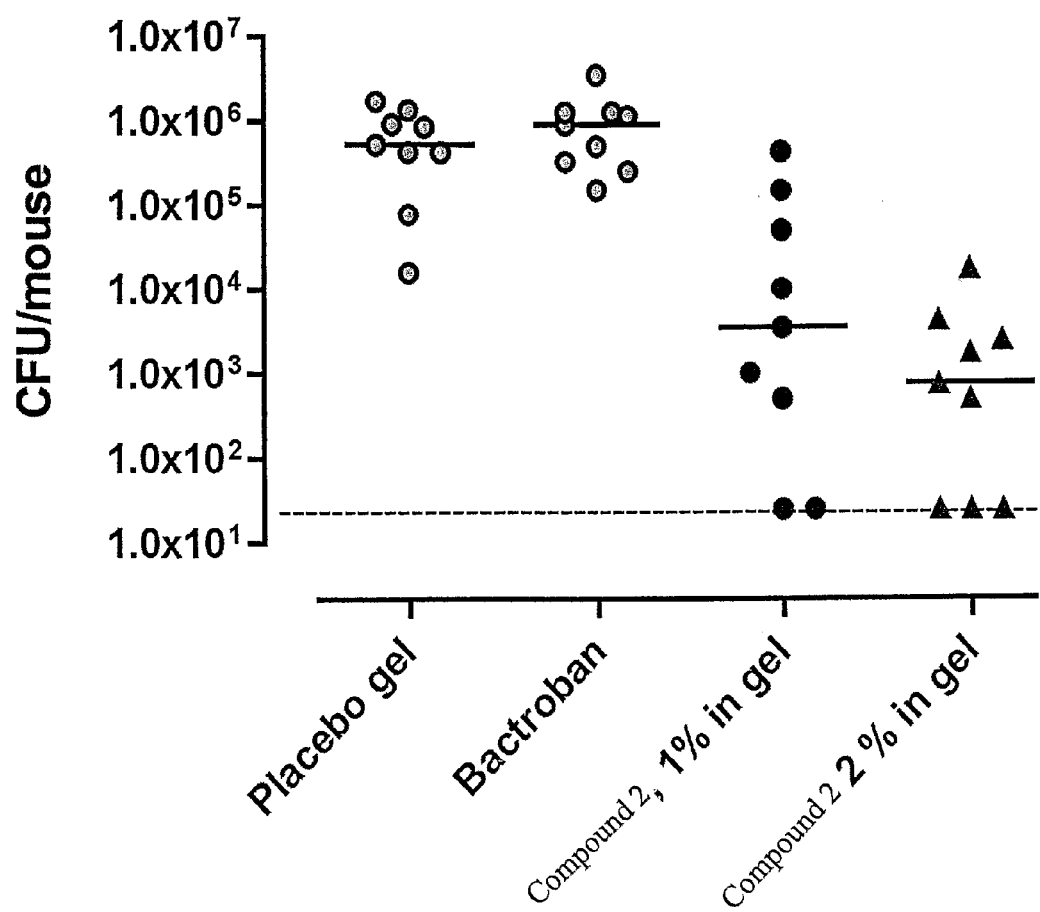
FIG. 2 is a graph showing the effect of one day topical treatment using compound 2 against *Streptococcus pyogenes* in a murine skin infection model. The number of colony forming units (CFU) are shown on the Y-axis and the type of topical treatment applied to the mice is shown on the X-axis.

The skin of mice was infected with *Staphylococcus aureus* or *Streptococcus pyogenes* and subsequently given a total of three treatments at three hourly intervals. Three hours after the last treatment, skin biopsies were collected and the number of colony forming units (CFUs) present in the skin sample was determined. Results are shown in FIGS. 1 and 2, expressed as the number of colony forming units per mouse.

In experiment 1 (FIG. 1), compound 2 was applied to the murine skin as part of either a cream or a gel containing 2% (w/w) of compound 2. The same cream or gel without compound 2 was used as a negative control (placebo). It can clearly be seen that the number of CFUs was reduced when a cream or gel containing compound 2 was applied to the murine skin, compared to the negative control, indicating that compound 2 exerted an antimicrobial effect against *Staphylococcus aureus*. The nature of the carrier, cream or gel, had no significant effect.

In experiment 2 (FIG. 2), compound 2 was applied in two different concentrations, as either a 1% or a 2% gel. A placebo gel and a known antibacterial "bactroban" were used as controls. It can be seen that gels containing compound 2 were more effective at reducing the number of CFUs than the placebo gel or the bactroban. The gel containing 2% of compound 2 was more effective than the gel containing only 1% of compound 2.

Example 5

Ex Vivo Efficacy of Compound 2 Against *Tricophyton Rubrum* in an Infected Nail Model The aim of this study was to measure the antifungal efficacy of Compound 2 (as defined in Example 1) for the treatment of onychomycosis and to compare it to commercially

TABLE 4

List of materials used in study

| Materials | Supplier |
|---|---|
| Amphotericin B | Sigma, UK |
| ATP Standards | Sigma, UK |
| BacTiter-Glo ™ | PROMEGA, UK |
| Ethanol | Fisher, UK |
| Sabouraud Dextrose Agar | Oxoid, UK |
| Ringers solution | Oxoid, UK |
| Terbinafine hydrochloride | Hetero Labs Limited, India |
| Tween 80 | Merck, Germany |

Test Systems
ChubTur® System
The ChubTur® test system is designed by MedPharm.
The ChubTur® test system was set up using *T. rubrum* as the test fungus, the source details for which are described below.
The ChubTur® test systems were set up at ambient temperature. However, incubation of the final cells is at 25±2° C.

*T. Rubrum*

A Sabouraud dextrose agar (SDA) slope inoculated with *T. rubrum* was obtained from Cardiff University. The culture was originally isolated from an onychomycotic patient. Upon receipt the organism was sub-cultured onto fresh SDA slopes at 25° C. for 7 days and reference samples were placed into a glycerol solution and cryogenically frozen. The organism has been sub-cultured on a three monthly basis to maintain viability. The cultures are stored at 25° C. for seven days after sub-culturing, and then stored 2-8° C. until required.

Methods
Preliminary Investigation
Preparation of Compound 2
A saturated solution of the Compound 2 was prepared using 10 mg of Compound 2 in 1 ml of De-ionised water.

After stirring overnight the mixture was centrifuged at 13,000 rpm for 5 min and the resulting supernatant decanted and stored at 2-8° C. for no more than 14 days.

The placebo was de-ionised water alone.

Preparation of Organism Suspensions

Preparation of Sabouraud Dextrose Agar

Briefly, 65 g of powdered SDA was added to 1 L de-ionised water. The mixture was heated until the agar visibly dissolved. It was then sterilised at 121° C. for 15 min in an autoclave, allowed to cool to 56° C., before transferring 25 ml into sterile 90 mm Petri dishes. The Petri dish was left with the lid slightly ajar (ca. 1 cm opening) for 30 min under a laminar flow cabinet before use.

Preparation of Ringer's Solution

Ringer's solution was prepared as described in SOP 3080. The solution was then sterilised in an autoclave for 15 min at 121° C.

Preparation of a Suspension of *T. Rubrum*
(i) A 90 mm SDA plate was seeded with *T. rubrum* by gently removing mycelium and spores using a sterile swab from a slope culture and transferring them onto the surface of the agar.
(ii) The agar plate was then incubated at 25° C. for 7 days.
(iii) The white spores were then washed from the surface of the plate with Ringers solution (20 ml).
(iv) The spore suspension was then filtered through a sterile gauze (Smith+Nephew, Propax, 7.5 cm×7.5 cm 8 ply gauze swab, BP Type 13) to remove mycelium and agar debris.
(v) A viable count of the spore suspension was performed and the spore count adjusted to approximately $1 \times 10^7$ cfu/ml, by diluting or concentrating the spores accordingly in a final volume of 20 ml.

Nail Preparation

Prior to cutting the distal human nails into 3 mm×3 mm segments, the nails were removed from the freezer and placed in a laminar flow cabinet for 30 min to equilibrate at room temperature. Following this the nails were briefly washed separately as follows:
(i) The nails were immersed into a 70% ethanol in water solution and vortex mixed for 1 min.
(ii) The ethanol solution was decanted and replaced with a fresh 70% ethanol solution and vortex mixed for a further min.
(iii) The ethanol solution was decanted and replaced with Ringer's solution, vortex mixed for 1 min and decanted and replaced with fresh Ringer's. This process of washing with Ringer's was carried out three times, replacing the wash solution at each phase.
(iv) Once the washing process was complete, the nails were placed in to a sterile Petri dish without a lid and air dried under a laminar flow cabinet for 30 min at room temperature.

Method Description: ChubTur® Cells

The ChubTur® cells were used as follows:
(i) After the nails were prepared, the thickness of each nail was measured using callipers prior to assembling into the ChubTur® cells.
(ii) The nail segments were initially inoculated on the underside with *T. rubrum* (5 µL of ~$1 \times 10^7$ cfu/ml), dried in a laminar flow cabinet and then mounted into a ChubTur® cell dorsal side up. The receptor chamber (4.4±0.24 cm$^3$ in volume) content was half filled with sterile Ringer's solution.
(iii) The cells were then incubated at 25±3° C. for 14 days to allow full growth of the organism on the nail.
(iv) At 14 days, the ChubTur® cells were removed from incubation and 10 µL of Compound 2 and Loceryl® were applied separately to the surface of the nail opposite to the side where the nails were inoculated with the organism suspension. Once the Compound 2 and Loceryl® had been applied to the surface of the nails, the cells were returned to incubation at 25±3° C.
(v) A multiple dosing regime where cells were dosed at 24 h intervals for 5 days was employed (Table 5). Before dosing, the surface of the nails was washed with sterile Ringer's solution to remove any excess Compound 2 and Loceryl® from the previous dose. Once this was done, a fresh 10 µL dose Compound 2 and Loceryl® was then applied to the appropriate cells according to the dosing regime in table 5.

TABLE 5

Table showing summary of samples to be investigated:

| Experimental Set-ups | Test item | Dose regimen |
|---|---|---|
| A (n = 3) | Compound 2 | Daily for 5 days |
| B (n = 3) | Loceryl ® | |
| C (n = 3) | Placebo | |
| D (n = 2) | Infected Control | — |
| E (n = 2) | Non-infected Control | — |

(vi) After the 5 day dosing, the excess of Compound 2 and Loceryl® where possible was removed from the surface of the nails and the nails were dismantled from the gasket in the ChubTur® cells. The nails were then analysed for the presence of ATP from the viable fungi.

Results and Discussion

Interference Investigation: Quenching Effect in the Presence of Formulation.

Figure 3:
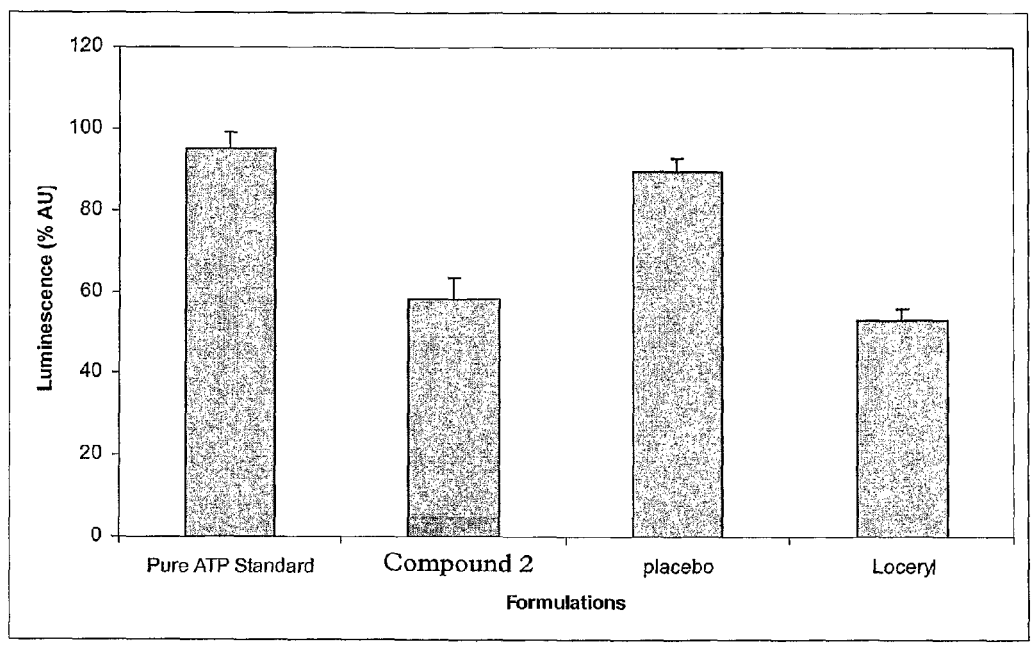
FIG. 3 is a graph showing a comparison of ATP recovery after quenching induced by formulations and their comparison to standards of known concentration (Example 5).

Any quenching effect from the Test Items was tested by adding 10 µL of Compound 2, Loceryl® and placebo to ATP calibration standard of known concentration (n=3) and comparing it against the standard alone (containing no Test Items). A linear regression curve was generated showing concentration against luminescence units for ATP calibration standards in the range 10 mg/mL to 1000 ng/mL. The comparison between ATP standard in the presence of various matrices is presented in FIG. 3. It can be observed from the graph that Compound 2 and Loceryl showed quenching when added to a known concentration of ATP standard solution (750 ng/mL) as the absorbance unit for the two formulations showed a marked decrease compared to the standard alone. The placebo showed no quenching effect as there was no marked difference between the placebo and standard alone.

ATP Recovery after Drug Application

Figure 4:
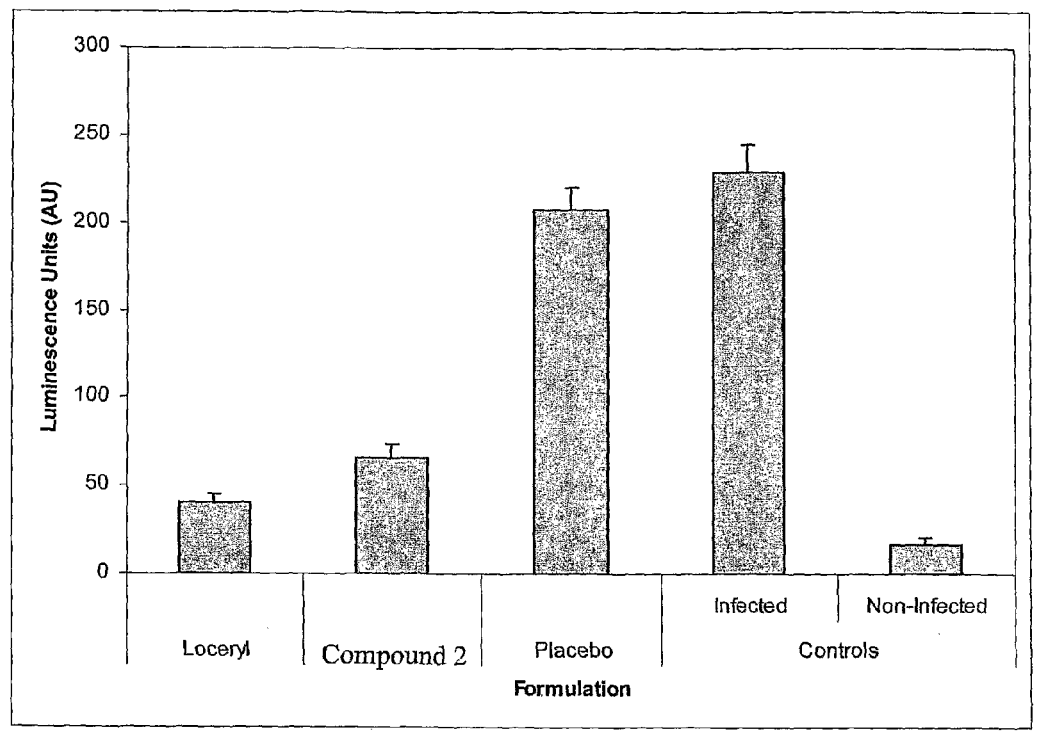
FIG. 4 is a graph showing a comparison of ATP release after application of different formulations (Example 5).

FIG. 4 shows the variation in ATP release from infected nail samples on application of Test Items (n=3) and their comparison with un-treated infected and un-treated non-infected control nail samples (controls were tested at n=2). It should be noted that the lower the amount of ATP recovered, the higher the efficacy of the Test Item against the test organism. It can be observed from the graph that the un-treated infected control produced an expectedly high ATP recovery whilst the untreated non-infected control produced very low levels of ATP. Compound 2 and Loceryl® were also observed to produce low ATP recovery compared to the infected control and placebo, indicating high efficacy against the test organism. There was no marked difference between the placebo and the un-treated infected control.

Example 6

A further compound of the invention was prepared and Minimal Inhibitory Concentration (MIC) values obtained against a range of bacteria.

H-Arg-Tbt-Arg-NH(CH$_2$)$_2$(2-Br-phenyl)

Saponification of Boc-Arg-Tbt-Arg-OMe

LiOH.H$_2$O (373 mg, 8.9 mmol) was added to a colorless solution of BocArgTbtArg-OMe.2HCl (2.5 g, 2.9 mmol, prepared as described in WO 01/66147) in a H$_2$O (5 ml) THF (20 ml) mixture and the reaction was stirred at room temperature for 30 min during which it rapidly developed a yellow color Dilute HCl (52 ml) and saturated brine (35 ml) were added and the resulting mixture extracted with DCM. The DCM was evaporated and the organic material redissolved in DCM, dried over Na$_2$SO4, filtered and concentrated. Obtained mass of BocArgTbtArg-OH: 2.46 g, 93%.

PyBOP Mediated Coupling

The TFA salt of BocArgTbtArgCO$_2$H (365 mg, 0.35 mmol) was mixed with 2-bromo phenyl ethyl amine (53 µl) in DMF (0.9 ml) and DIPEA (120 µl) was added. The reaction mixture was stirred at room temperature for 5 min before PyBOP (194 mg, 0.37 mmol) was added and then left for 3 hours. Prior to the workup the mixture was diluted with EtOAc (20 ml) and washed with 2×30 ml 5% citric acid sol., 2×30 ml 5% NaHCO$_3$ sol., 30 ml sat.brine, followed by drying over Na$_2$SO$_4$, filtration and concentration. The crude product was isolated as an oil (432 mg) containing a byproduct from the coupling reagent. The Boc group was removed by dissolving the crude in 15 ml 4 M HCl in 1,4-dioxane and stirring it for 30 min at room temperature before concentration and final purification by reversed phase chromatography.

Purity: >95%, Electrospray mass spectrometry (m/z, protonated molecular ion): 866.48/868.56 (calculated), 866.5/868.5 (observed).

Microbiological Data

Minimal inhibitory concentration (mg/l), H-Arg-Tbt-Arg-NH—Y—Z

| Y-Z | E. coli | S. aureus | MRSA | Str. pyogenes |
|---|---|---|---|---|
| —(CH$_2$)$_2$—(2-BrPh) | 6 | 3 | 3 | 3 |

The invention claimed is:

1. A compound of formula (I)

$$AA\text{-}AA\text{-}AA\text{-}X\text{—}Y\text{—}Z \quad (I)$$

wherein, in any order, 2 of said AA (amino acid) moieties are cationic amino acids and 1 of said AA is an amino acid with a lipophilic R group, the R group having 14-27 non-hydrogen atoms;

X is a N atom, which may be substituted by a branched or unbranched C$_1$-C$_{10}$ alkyl or aryl group which group may incorporate up to 2 heteroatoms selected from N, O and S;

Y represents —R$_a$—R$_b$— wherein

R$_a$ is C, O, S or N, and

R$_b$ is C; each of R$_a$ and R$_b$ may be substituted by C$_1$-C$_4$ alkyl groups or unsubstituted; and Z is a group comprising 1 to 3 cyclic groups each of 5 or 6 non-hydrogen atoms, 2 or more of the cyclic groups may be fused and one or more of the cyclic groups may be substituted; the Z moiety incorporates as maximum of 15 non-hydrogen atoms; and wherein the bond between Y and Z is a covalent bond between R$_a$ or R$_b$ of Y and a non-hydrogen atom of one of the cyclic groups of Z.

2. The compound of formula (I) as claimed in claim 1 which is a peptide.

3. The compound of formula (I) as claimed in claim 1 in which said cationic amino acids are lysine and/or arginine.

4. The compound of formula (I) as claimed in claim 1 wherein the lipophilic R group contains 2 or more cyclic groups which may be fused or connected.

5. The compound of formula (I) as claimed in claim 1 wherein X is unsubstituted.

6. The compound of formula (I) as claimed in claim 1 wherein R$_a$ is C.

7. The compound of formula (I) as claimed in claim 1 wherein Y is —R$_a$—R$_b$— and unsubstituted.

8. The compound of formula (I) as claimed in claim 7 wherein Y is —CH$_2$—CH$_2$—.

9. The compound of formula (I) as claimed in claim 1 wherein Z is phenyl.

10. The compound as claimed in claim 1 being of formula (II)

$$AA_1\text{-}AA_2\text{-}AA_1\text{-}X\text{—}Y\text{—}Z \quad (II)$$

wherein:

AA$_1$ is a cationic amino acid; and

AA$_2$ is an amino acid with a lipophilic R group, the R group having 14-27 non-hydrogen atoms.

11. The compound of formula (I) as claimed in claim 1 in which the amino acid with a lipophilic R group is selected from tributyl tryptophan (Tbt) and a biphenylalanine derivative selected from Phe (4-(2-Naphthyl)), Phe (4-(1-Naphthyl)), Bip (4-n-Bu), Bip (4-Ph) and Bip (4-T-Bu).

12. The compound as claimed in claim 1 in which —X—Y—Z together are —NHCH$_2$CH$_2$Ph.

13. The compound as claimed in claim 1 having the structural formula

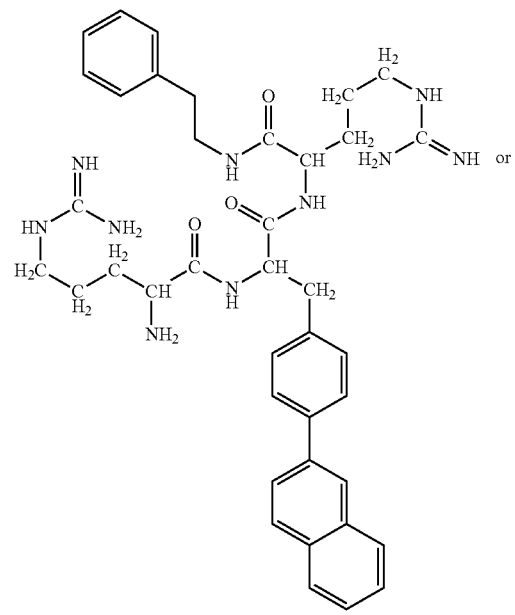

-continued

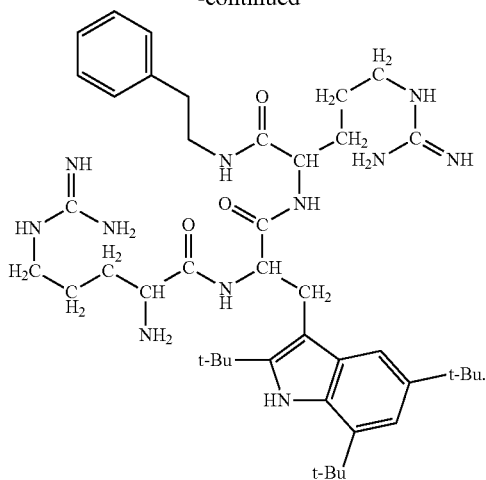

14. A method of treating a microbial or fungal infection comprising administering the compound as claimed in claim 1 to a patient in need of such treatment.

15. A formulation comprising a compound as claimed in claim 1 in admixture with a suitable diluent, carrier or excipient.

16. The formulation as claimed in claim 15 which is a pharmaceutical formulation.

17. The formulation as claimed in claim 16 which is suitable for topical administration.

18. The compound of claim 10 in which $AA_2$ is selected from tributyl tryptophan (Tbt) and a biphenylalanine derivative selected from Phe (4-(2-Naphthyl)), Phe (4-(1-Naphthyl)), Bip (4n-Bu), Bip (4-Ph) and Bip (4-T-Bu).

* * * * *